United States Patent [19]
Sugii et al.

[11] Patent Number: 5,808,086
[45] Date of Patent: Sep. 15, 1998

[54] PROCESS FOR PREPARING BIS (2-HYDROXYPHENYL-3-BENZTRIAZOLE) METHANES

[75] Inventors: Naoyuki Sugii, Iwaki; Toshiyuki Yamauchi, Tokyo; Eisuke Kanagawa, Kitamoto; Hideo Aoki; Kazuyuki Ishihara, both of Toda, all of Japan

[73] Assignee: Johoku Chemical Co., Ltd., Tokyo, Japan

[21] Appl. No.: 901,347

[22] Filed: Jul. 28, 1997

[30] Foreign Application Priority Data

Jul. 31, 1996 [JP] Japan ................................. 8-202251

[51] Int. Cl.$^6$ .................................................. C07D 249/20
[52] U.S. Cl. ........................................... 548/260; 548/259
[58] Field of Search ...................................... 548/259, 260

[56] References Cited

U.S. PATENT DOCUMENTS 3,936,305  2/1976  Hiraishi et al. .
5,237,071  8/1993  Leistner et al. .

FOREIGN PATENT DOCUMENTS 141206    11/1970  Czechoslovakia .
0180991    5/1986  European Pat. Off. .
0180993    5/1986  European Pat. Off. .
0180993A2  5/1986  European Pat. Off. .
0490815A1  6/1992  European Pat. Off. .
1670951    2/1971  Germany .
4118545A1 12/1992  Germany .
458468B2   9/1992  Japan .
5213908A   8/1993  Japan .

OTHER PUBLICATIONS

Chemical Abstracts 62720h, vol. 77, No. 10, Columbus, Ohio, US; p. 28; XP002045035; Sep. 4, 1992.

Chemical Abstracts 19629q, vol. 79, No. 4, Columbus, Ohio, US; p. 38; XP002045036; Jul. 30, 1973.

Patent Abstracts of Japan, vol. 10, No. 303 (C–378), Oct. 16, 1986 which corresponds to JP 61 118373 A.

Primary Examiner—Patricia L. Morris
Attorney, Agent, or Firm—Birch, Stewart, Kolasch & Birch, LLP

[57] ABSTRACT

A 2-hydroxyphenylbenzotriazole is reacted with a formaldehyde and an amino alcohol in an organic solvent in the presence of a basic catalyst. It is thereby possible to obtain bis(2-hydroxyphenyl-3-benzotriazole) methanes efficiently and at a high yield.

5 Claims, No Drawings

PROCESS FOR PREPARING BIS (2-HYDROXYPHENYL-3-BENZTRIAZOLE) METHANES

BACKGROUND OF THE INVENTION

1. Field of the Invention

The present invention relates to a novel process for preparing bis(2-hydroxyphenyl-3-benzotriazole) methanes which are useful as ultraviolet absorbers for rubber, plastics and photographic layers.

2. Description of the Related Art

Hydroxyphenylbenzotriazoles themselves are commonly known as ultraviolet absorbers, and methylene bis-type compounds prepared by dimerizing these with methylene bonds are also publicly known as ultraviolet absorbers. Methylene bis-type compounds and processes for their preparation are described in Czechoslovakian Patent No. 141,206, German Patent No. 1,670,951, U.S. Pat. No. 3,936,305, Japanese Examined Patent Publication No. 4-58468 (corresponding to European Patent Publication No. 0180993A2) and Japanese Unexamined Patent Publication No. 5-213908.

For example, Czechoslovakian Patent No. 141,206 describes a process for dimerizing hydroxyphenylbenzotriazoles with aqueous formalin in a reaction solution, and German Patent No. 1,670,951 describes a process for dimerizing them with paraformaldehyde in the presence of glacial acetic acid or sulfuric acid. In addition, Japanese Unexamined Patent Publication No. 5-213908 describes a process for dimerizing with paraformaldehyde or trioxane in concentrated sulfuric acid. With this process the yield of the desired product is higher than that of the former two processes, but it is still insufficient and is in need of improvement.

Also, Japanese Examined Patent Publication No. 4-58468 (corresponding to European Patent Publication No. 0180993A2) describes a process involving a 2-step reaction of synthesizing an intermediate (II) from a starting compound (I) with a lower alkylamine and formaldehyde in a solvent, and then dimerizing it to produce the desired product (III), as illustrated by the following reaction formula.

wherein X represents a hydrogen atom, halogen atom, alkyl group, allyl group or alkoxy group, R represents an alkyl group or arylalkyl group, and Alk represents a lower alkyl group.

Although this process gives higher yields compared to the aforementioned three processes, there is demand for even greater improvement in the yield as well as a shortening of the process.

SUMMARY OF THE INVENTION

As a result of diligent research aimed at overcoming these problems, the present inventors have completed the present invention upon the finding that bis(2-hydroxyphenyl-3-benzotriazole) methanes, which are methylene bis-type compounds, can be obtained in a quick and simple manner at a high yield by using formaldehydes and amino alcohols in the presence of basic catalysts.

Thus, the present invention provides a process which allows bis(2-hydroxyphenyl-3-benzotriazole) methanes to be obtained efficiently and at a high yield.

In other words, the present invention provides a process for preparing a bis(2-hydroxyphenyl-3-benzotriazole) methane which is characterized by reacting a 2-hydroxyphenylbenzotriazole with a formaldehyde and an amino alcohol in an organic solvent in the presence of a basic catalyst.

DESCRIPTION OF THE PREFERRED EMBODIMENTS

According to the process of the invention, the 2-hydroxyphenylbenzotriazole used as the starting material is typically a compound which is represented by the following general formula (1):

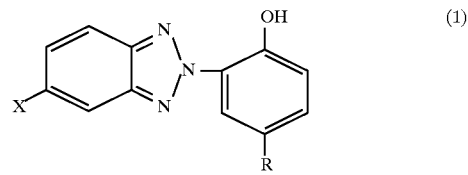

wherein X represents a hydrogen atom, halogen atom, alkyl group, allyl group or alkoxy group and R represents an alkyl group or arylalkyl group.

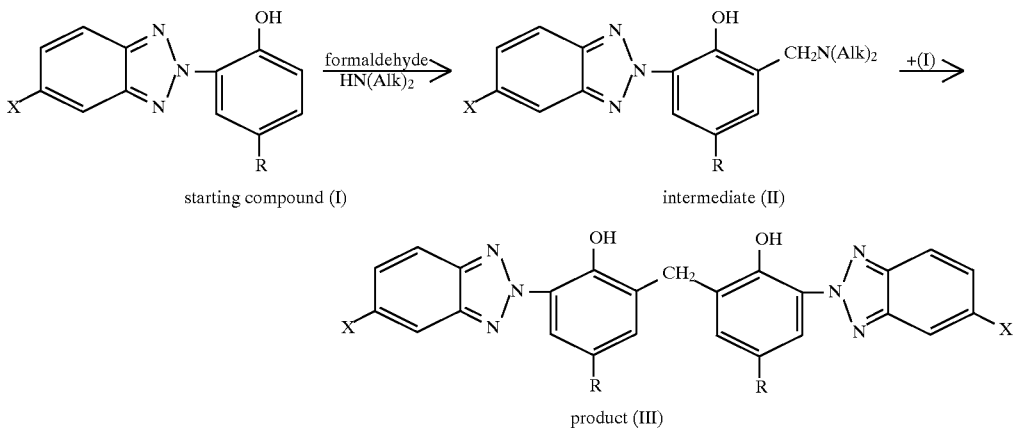

starting compound (I)

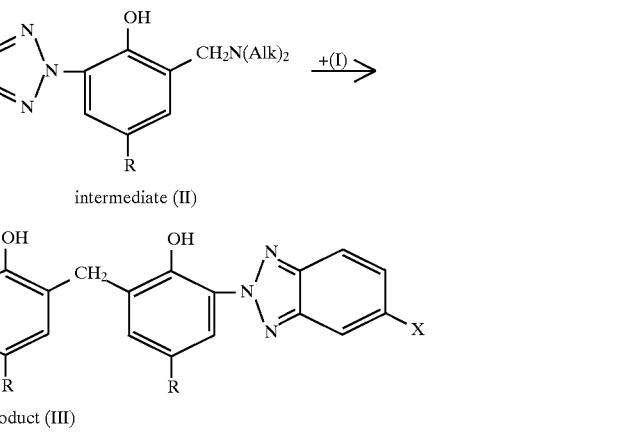

intermediate (II)

product (III)

Consequently, the bis(2-hydroxyphenyl-3-benzotriazole) methane which is the object compound of the process of the invention is a methylene bis-type compound typically represented by the following general formula (3):

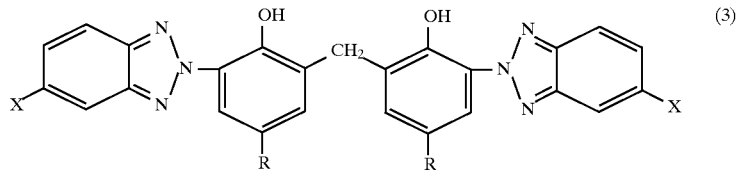

(3)

wherein X each independently represents a hydrogen atom, halogen atom, alkyl group, allyl group or alkoxy group and each R independently represents an alkyl group or arylalkyl group.

The process of the invention is characterized by using a formaldehyde together with an amino alcohol. "Amino alcohol" is a general term for amine derivatives with an alcoholic hydroxyl group, and these are also known as alkamines. According to the invention it is particularly suitable to use primary and secondary amino alcohols represented by the following general formula (2):

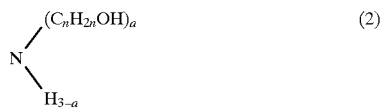

(2)

wherein n is an integer of 1 or greater, and a is 1 or 2.

As examples of such amino alcohols there may be mentioned monoethanolamine, monopropanolamine, monobutanolamine, diethanolamine, dipropanolamine and dibutanolamine which are readily obtainable in the industry at the current time, but of course there is no limitation to these.

As useful formaldehydes according to the invention there may be mentioned, for example, formaldehyde, paraformaldehyde, trioxane and tetraoxymethylene.

As basic catalysts there may be used alkali metals, alkaline earth metals and their hydroxides, oxides, hydrides, carbonates, amides and alcoholates.

An organic solvent may be used as the reaction solvent, and there are no particular restrictions here so long as it is an organic solvent which does not react with the reactants. As examples of useful organic solvents there may be mentioned aliphatic hydrocarbons, aromatic hydrocarbons, halogenated hydrocarbons and common alcohols or ethers, among which alcohols and ethers are most suitable.

The reaction is preferably accomplished by mixing and dissolving the 2-hydroxyphenylbenzotriazole, formaldehyde and amino alcohol in the organic solvent and heating and stirring the mixture at 70°–200° C. for 1 to 10 hours in the presence of the basic catalyst. After removal of the amino alcohol and solvent under reduced pressure, the bis(2-hydroxyphenyl-3-benzotriazole) methane may be obtained as the desired dimerized product. Here, the formaldehyde may be used in an amount of 0.5–2 moles, and preferably 0.5–1 mole in terms of formaldehyde and the amino alcohol may be used in an amount of 0.1–2 moles, and preferably 0.1–1 mole, with respect to one mole of the 2-hydroxyphenylbenzotriazole. The amount of the formaldehyde is preferably a stoichiometric amount of 0.5 moles or greater in terms of formaldehyde with respect to one mole of the 2-hydroxyphenylbenzotriazole, but if it exceeds one mole there is a tendency for the reaction product to contain many high molecular weight impurities. The amount of the amino alcohol does not need to be the equivalent of 0.5 mole or greater with respect to the formaldehyde since it is not a 2-stage reaction with intermediates, but at lower than 0.1 mole the reaction essentially fails to proceed, while at greater than 1 mole there is a tendency for the yield to gradually decrease.

The Mannich reaction is well-known as a reaction for obtaining aminomethylated intermediates from phenols, formaldehydes and alkylamines as disclosed in Japanese Examined Patent Publication No. 4-58468 mentioned above, and such aminomethylated intermediates are called Mannich bases. However, in the process of the present invention virtually no corresponding Mannich bases are produced, and directly dimerized products are obtained from 2-hydroxyphenylbenzotriazoles. Also, since the processes described above which use alkylamines are 2-stage reactions involving synthesis of Mannich bases followed by dimerization, the intermediates have a high possibility of impurities and high molecular weight by-products are produced as a result of the long reaction times; however, since the process of the invention does not involve intermediates, the object product may be obtained at a high yield with simple steps and in a short time.

The present invention will now be explained in more detail by way of examples.

EXAMPLE 1

After 323 g of 2-(2'-hydroxy-5'-t-octylphenyl) benzotriazole, 217 g of 98% di(ethanol)amine, 18 g of 86% paraformaldehyde and 11 g of sodium hydroxide were heated to dissolution in 390 g of n-octanol at 70°–100° C. for 60 minutes while stirring, the temperature of the mixture was gradually raised and the resulting water was recovered.

When the temperature of the reaction mixture reached 180°–190° C., the reaction was continued for another 3 hours. After completion of the reaction, the solvent was removed under reduced pressure and then 350 g of xylene was added for dissolution of the product at a reflux temperature of 130°–140° C. After dissolution, the solution was cooled to obtain a crude product as crystals. The crude crystals obtained by filtration were analyzed by liquid chromatography and found to have a purity of 98% (90% yield). The crude crystals were then recrystallized from the xylene to obtain a purified product of a light yellow-white powder with a melting point of 198° C. The purity of this purified product was determined by liquid chromatography analysis to be 100%.

As a result of elemental analysis of the C, H, N and O in the purified product, it was confirmed to be the target substance on the basis of the nearly theoretical values obtained as shown below.

|   | calculated (%) | found (%) |
|---|---|---|
| C | 74.6 | 74.9 |
| H | 7.7 | 7.5 |
| N | 12.7 | 12.6 |
| O | 4.8 | 4.9 |

EXAMPLE 2

The procedure of Example 1 was repeated, except that 42 g of 98% monoethanolamine was used instead of di(ethanol)amine.

The resulting crude crystals were analyzed by liquid chromatography and found to have a purity of 98% (90% yield). The crude crystals were then recrystallized from the xylene to obtain a purified product of a light yellow-white powder with a melting point of 198° C. The purity of this purified product was determined by liquid chromatography analysis to be 100%.

As a result of elemental analysis of the C, H, N and O in the purified product, it was confirmed to be the target substance on the basis of the nearly theoretical values obtained as shown below.

|   | calculated (%) | found (%) |
|---|---|---|
| C | 74.6 | 74.7 |
| H | 7.7 | 7.8 |
| N | 12.7 | 12.6 |
| O | 4.8 | 4.8 |

EXAMPLE 3

After 58 g of 2-(2'-hydroxy-5'-methylphenyl)benzotriazole, 11 g of monoethanolamine, 5 g of 86% paraformaldehyde and 5 g of potassium hydroxide were heated to dissolution in 150 g of n-octanol at 70°–100° C. for 60 minutes while stirring, the temperature of the mixture was gradually raised and the resulting water was recovered.

When the temperature of the reaction mixture reached 180°–190° C., the reaction was continued for another 3 hours. After completion of the reaction, the solvent was removed under reduced pressure and then 300 g of xylene was added for dissolution of the product at a reflux temperature of 130°–140° C. After dissolution, the solution was cooled to obtain a crude product as crystals. The crude crystals obtained by filtration were analyzed by liquid chromatography and found to have a purity of 99% (85% yield). The crude crystals were then recrystallized from the xylene to obtain a purified product of a light yellow-white powder with a melting point of 285° C. The purity of this purified product was determined by liquid chromatography analysis to be 100%.

As a result of elemental analysis of the C, H, N and O in the purified product, it was confirmed to be the target substance on the basis of the nearly theoretical values obtained as shown below.

|   | calculated (%) | found (%) |
|---|---|---|
| C | 70.1 | 70.0 |
| H | 4.8 | 5.0 |
| N | 18.2 | 18.0 |
| O | 6.9 | 6.8 |

EXAMPLE 4

After 74 g of 2-(2'-hydroxy-5'-isopropylphenyl)-5-chlorobenzotriazole, 11 g of monoethanolamine, 5 g of 86% paraformaldehyde and 5 g of sodium methylate were heated to dissolution in 150 g of n-octanol at 70°–100° C. for 60 minutes while stirring, the temperature of the mixture was gradually raised and the resulting water was recovered.

When the temperature of the reaction mixture reached 180°–190° C., the reaction was continued for another 3 hours. After completion of the reaction, the solvent was removed under reduced pressure and then 230 g of xylene was added for dissolution of the product at a reflux temperature of 130°–140° C. After dissolution, the solution was cooled to obtain a crude product as crystals. The crude crystals obtained by filtration were analyzed by liquid chromatography and found to have a purity of 99% (91% yield). The crude crystals were then recrystallized from the xylene to obtain a purified product of a light yellow-white powder with a melting point of 274° C. The purity of this purified product was determined by liquid chromatography analysis to be 100%.

As a result of elemental analysis of the C, H, N and O in the purified product, it was confirmed to be the target substance on the basis of the nearly theoretical values obtained as shown below.

|   | calculated (%) | found (%) |
|---|---|---|
| C | 63.4 | 63.3 |
| H | 4.8 | 4.9 |
| N | 14.3 | 14.1 |
| O | 5.4 | 5.5 |
| Cl | 12.1 | 11.9 |

EXAMPLE 5

After 69 g of 2-(2'-hydroxy-5'-t-butylphenyl)benzotriazole, 11 g of 98% monoethanolamine, 5 g of 86% paraformaldehyde and 5 g of sodium hydroxide were heated to dissolution in 100 g of n-octanol at 70°–100° C. for 60 minutes while stirring, the temperature of the mixture was gradually raised and the resulting water was recovered.

When the temperature of the reaction mixture reached 180°–190° C., the reaction was continued for another 3 hours. After completion of the reaction, the solvent was removed under reduced pressure and then 350 g of xylene was added for dissolution of the product at a reflux temperature of 130°–140° C. After dissolution, the solution was cooled to obtain a crude product as crystals. The crude crystals obtained by filtration were analyzed by liquid chromatography and found to have a purity of 99% (94% yield). The crude crystals were then recrystallized from the xylene to obtain a purified product of a light yellow-white powder with a melting point of 273° C. The purity of this purified product was determined by liquid chromatography analysis to be 100%.

As a result of elemental analysis of the C, H, N and O in the purified product, it was confirmed to be the target substance on the basis of the nearly theoretical values obtained as shown below.

|   | calculated (%) | found (%) |
|---|---|---|
| C | 72.4 | 72.6 |
| H | 6.2 | 6.4 |
| N | 15.3 | 15.2 |
| O | 5.7 | 5.8 |

EXAMPLE 6

After 167 g of 2-(2'-hydroxy-5'-t-octylphenyl)benzotriazole, 27 g of 98% monoisopropanolamine, 10 g of 86% paraformaldehyde and 8 g of sodium hydroxide were heated to dissolution in 200 g of diisopentyl ether at 70°–100° C. for 60 minutes while stirring, the temperature of the mixture was gradually raised and the resulting water was recovered.

When the temperature of the reaction mixture reached 160°–170° C., the reaction was continued for another 7 hours. After completion of the reaction, the solvent was removed under reduced pressure and then 180 g of xylene was added for dissolution of the product at a reflux temperature of 130°–140° C. After dissolution, the solution was cooled to obtain a crude product as crystals. The crude crystals obtained by filtration were analyzed by liquid chromatography and found to have a purity of 98% (80% yield). The crude crystals were then recrystallized from the xylene to obtain a purified product of a light yellow-white powder with a melting point of 198° C. The purity of this purified product was determined by liquid chromatography analysis to be 100%.

As a result of elemental analysis of the C, H, N and O in the purified product, it was confirmed to be the target substance on the basis of the nearly theoretical values obtained as shown below.

|   | calculated (%) | found (%) |
|---|---|---|
| C | 74.6 | 74.4 |
| H | 7.7 | 7.9 |
| N | 12.7 | 12.5 |
| O | 4.8 | 4.5 |

EXAMPLE 7

After 167 g of 2-(2'-hydroxy-5'-t-octylphenyl)benzotriazole, 112 g of 98% di(ethanol)amine, 10 g of 86% paraformaldehyde and 13 g of potassium carbonate were heated to dissolution in 200 g of di-n-hexyl ether at 70°–100° C. for 60 minutes while stirring, the temperature of the mixture was gradually raised and the resulting water was recovered.

When the temperature of the reaction mixture reached 180°–190° C., the reaction was continued for another 7 hours. After completion of the reaction, the solvent was removed under reduced pressure and then 180 g of xylene was added for dissolution of the product at a reflux temperature of 130°–140° C. After dissolution, the solution was cooled to obtain a crude product as crystals. The crude crystals obtained by filtration were analyzed by liquid chromatography and found to have a purity of 98% (82% yield). The crude crystals were then recrystallized from the xylene to obtain a purified product of a light yellow-white powder with a melting point of 198° C. The purity of this purified product was determined by liquid chromatography analysis to be 100%.

As a result of elemental analysis of the C, H, N and O in the purified product, it was confirmed to be the target substance on the basis of the nearly theoretical values obtained as shown below.

|   | calculated (%) | found (%) |
|---|---|---|
| C | 74.6 | 74.7 |
| H | 7.7 | 7.4 |
| N | 12.7 | 12.5 |
| O | 4.8 | 5.0 |

EXAMPLE 8

After 167 g of 2-(2'-hydroxy-5'-t-octylphenyl)benzotriazole, 22 g of 98% monoethanolamine, 10 g of 86% paraformaldehyde and 13 g of potassium carbonate were heated to dissolution in 200 g of 2-(2-methoxyethoxy)ethanol at 70°–100° C. for 60 minutes while stirring, the temperature of the mixture was gradually raised and the resulting water was recovered.

When the temperature of the reaction mixture reached 180°–190° C., the reaction was continued for another 5 hours. After completion of the reaction, the solvent was removed under reduced pressure and then 180 g of xylene was added for dissolution of the product at a reflux temperature of 130°–140° C. After dissolution, the solution was cooled to obtain a crude product as crystals. The crude crystals obtained by filtration were analyzed by liquid chromatography and found to have a purity of 98% (85% yield). The crude crystals were then recrystallized from the xylene to obtain a purified product of a light yellow-white powder with a melting point of 198° C. The purity of this purified product was determined by liquid chromatography analysis to be 100%.

As a result of elemental analysis of the C, H, N and O in the purified product, it was confirmed to be the target substance on the basis of the nearly theoretical values obtained as shown below.

|   | calculated (%) | found (%) |
|---|---|---|
| C | 74.6 | 74.9 |
| H | 7.7 | 7.5 |
| N | 12.7 | 12.6 |
| O | 4.8 | 4.9 |

REFERENCE EXAMPLE 1

Following the process described in Japanese Examined Patent Publication No. 4-58468, 32 g of 2-(2'-hydroxy-5'-t-octylphenyl)benzotriazole, 5 g of 86% paraformaldehyde and 11 g of diethylamine were dissolved in 25 ml of n-butanol and reacted for 24 hours while heating to reflux (95°–105° C.).

After completion of the reaction, the solvent was removed under reduced pressure to obtain a distillate to which 20 ml of xylene was added for dissolution, and then 6 g of sodium methylate (28% methanol solution) was added as a catalyst. Next, the temperature was raised to reflux temperature (140°–150° C.) while blowing in nitrogen gas, and the mixture was stirred for 10 hours. The solvent was then distilled off under reduced pressure to obtain 29 g of a crude product. The resulting crude product crystals were analyzed by liquid chromatography and found to have a purity of 70% (63% yield).

REFERENCE EXAMPLE 2

The procedure of Reference Example 1 was repeated, except that dibutylamine was used instead of diethylamine.

The resulting crude product crystals were analyzed by liquid chromatography and found to have a purity of 72% (60% yield).

REFERENCE EXAMPLE 3

Following the process described in Japanese Unexamined Patent Publication No. 5-213908, 97 g of 2-(2'-hydroxy-5'-t-octylphenyl)benzotriazole was added to 185 g of 98% concentrated sulfuric acid, and after cooling the mixture to below 30° C., 4.5 g of 86% paraformaldehyde was gradually added over 60 minutes. The reaction was continued for 5 hours at this temperature. Next, 100 ml of monochlorobenzene was added to the reaction mixture, and 300 ml water was added while continuing the cooling. Washing was then repeated with warm water at 90° C. until the pH reached neutral.

The resulting reaction mixture was cooled to 10° C. to obtain crystals, and after filtering the crystals were taken out and dried. The resulting crude product crystals were analyzed by liquid chromatography and found to have a purity of 80% (55% yield).

REFERENCE EXAMPLE 4

After 80 g of 2-(2'-hydroxy-5'-t-octylphenyl) benzotriazole, 13 g of 86% paraformaldehyde, 28 g of diethylamine and 5 g of sodium methylate were heated to dissolution in 100 g of n-octanol at 70°–100° C. for 60 minutes while stirring, the temperature of the mixture was gradually raised and the resulting water was recovered.

When the temperature of the reaction mixture reached 180°–190° C., the reaction was continued for another 3 hours. After completion of the reaction, the solvent was removed under reduced pressure and then 350 g of xylene was added for dissolution of the product at a reflux temperature of 130°–140° C. After dissolution, the solution was cooled to obtain a crude product as crystals. The crude crystals obtained by filtration were analyzed by liquid chromatography and found to have a purity of 95% (23% yield).

Based on the results of liquid chromatography analysis of the crude product crystals, they were found to be different from those of Examples 1 and 2 in that there was very little production of the target product and a large amount of residual intermediate Mannich base compounds were present.

We claim:

1. A process for preparing a bis(2-hydroxyphenyl-3-benzotriazole) methane which is characterized by reacting a 2-hydroxyphenylbenzotriazole with a formaldehyde and an amino alcohol in an organic solvent in the presence of a basic catalyst.

2. The process of claim 1, wherein the 2-hydroxyphenylbenzotriazole is represented by the following general formula (1):

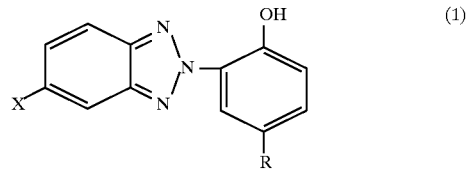

wherein X represents a hydrogen atom, halogen atom, alkyl group, allyl group or alkoxy group and R represents an alkyl group or arylalkyl group.

3. The process of claim 1, wherein the formaldehyde is selected from among formaldehyde, paraformaldehyde, trioxane and tetraoxymethylene.

4. The process of claim 1, wherein the amino alcohol is represented by the following general formula (2):

wherein n is an integer of 1 or greater, and a is 1 or 2.

5. The process of claim 1, wherein the bis(2-hydroxyphenyl-3-benzotriazole) methane is represented by the following general formula (3):

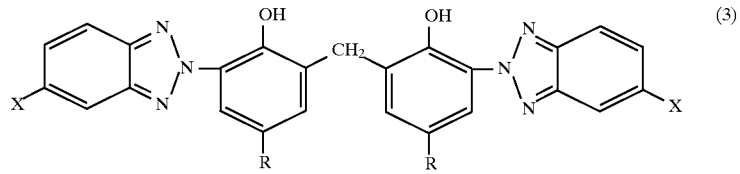

wherein X each independently represents a hydrogen atom, halogen atom, alkyl group, allyl group or alkoxy group and each R independently represents an alkyl group or arylalkyl group.

* * * * *